(12) United States Patent
Tayebi

(10) Patent No.: US 8,382,927 B1
(45) Date of Patent: Feb. 26, 2013

(54) METHOD OF AND APPARATUS FOR REINFORCING MEDICAL BALLOONS

(76) Inventor: Amad Tayebi, Westford, MA (US)

( * ) Notice: Subject to any disclaimer, the term of this patent is extended or adjusted under 35 U.S.C. 154(b) by 327 days.

(21) Appl. No.: 12/924,389

(22) Filed: Sep. 27, 2010

Related U.S. Application Data

(63) Continuation-in-part of application No. 11/809,525, filed on Jun. 1, 2007, now Pat. No. 7,803,240.

(60) Provisional application No. 60/809,941, filed on Jun. 1, 2006.

(51) Int. Cl.
*B32B 37/00* (2006.01)

(52) U.S. Cl. .......................... 156/148; 156/149; 156/171

(58) Field of Classification Search .................. 156/149, 156/148, 171, 169, 173, 175
See application file for complete search history.

(56) References Cited

U.S. PATENT DOCUMENTS 7,803,240 B1 * 9/2010 Tayebi .......................... 156/149

* cited by examiner

*Primary Examiner* — Jeff Aftergut
(74) *Attorney, Agent, or Firm* — Amad Tayebi; American Patent Associates

(57) ABSTRACT

A method is provided for reinforcing medical balloons in order to withstand high internal pressures without excessive dilation of the reinforced balloon. The method calls for the use of a tubular reinforcement sleeve and a device designed for holding the balloon, stretching the reinforcement sleeve, application of yarn wrappings around the reinforcement sleeve, application of adhesive and curing the adhesive.

1 Claim, 1 Drawing Sheet

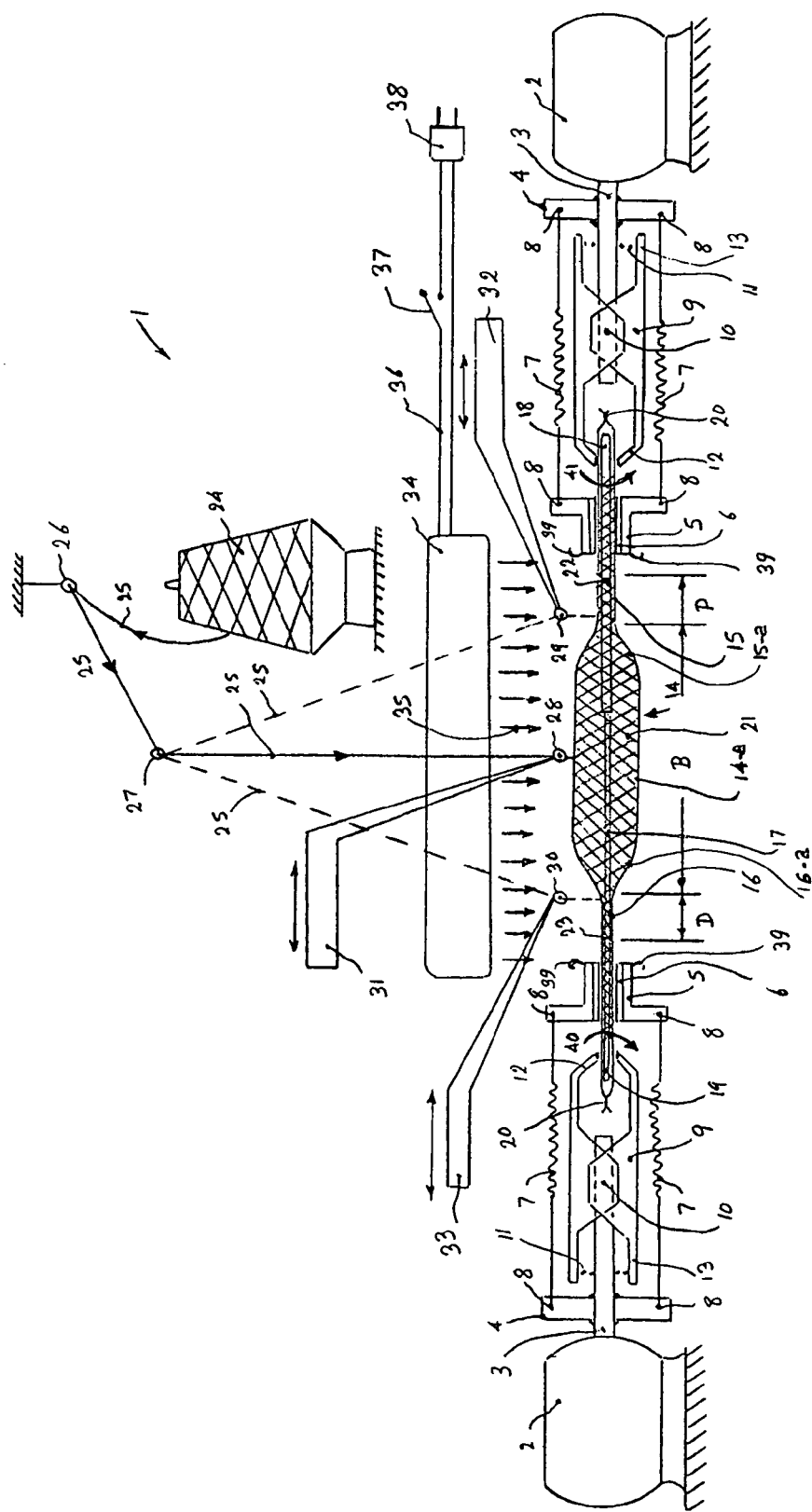

US 8,382,927 B1

METHOD OF AND APPARATUS FOR REINFORCING MEDICAL BALLOONS

This Continuation-in-Part application claims priority of application Ser. No. 11/809,525 filed on Jun. 1, 2007 which is scheduled to be issued on Sep. 28, 2010 as U.S. Pat. No. 7,803,240. This application incorporates, by reference, application Ser. No. 11/809,525, in its entirety.

Application Ser. No. 11/809,525 claims priority of Provisional Application No. 60/809,941, filed on Jun. 1, 2006 and incorporated, by reference, said Provisional Application in its entirety. This application also claims priority of Provisional Application 60/809,941 and incorporates, by reference, said Provisional Application in its entirety.

FIELD OF THE INVENTION

The present invention is in the field of medical balloons. In particular, it teaches and claims methods of and apparatus for reinforcing medical balloons and reinforced medical balloons made accordingly which are capable of withstanding high internal pressures without bursting and without excessive dilation (expansion or increasing its dimensions) longitudinally and laterally. More particularly, the balloons made in accordance with the present invention exhibit a low dilation (increase in their dimensions), (lower than 10%), laterally and longitudinally under high internal pressures. As such, the balloons, made in accordance with the present invention, are particularly suitable for use in balloon-tipped catheters where a collapsed wire stent is placed around the collapsed (deflated) balloon, the catheter is threaded through an artery to the location of the blockage. The balloon is then inflated in order to expand the stent surrounding it against the sides of the arterial wall. The balloon is then deflated, leaving the expanded stent in place against the artery wall and the catheter is removed.

BACKGROUND OF THE INVENTION

The prior art teaches and describes a variety of structures, methods and devices for making reinforced balloons for medical applications. Such structures, methods and devices are described in U.S. Pat. Nos. 4,490,421, Re. 33,561, Re. 32,983, 6,156,254, 5,201,706, 5,647,848, 4,706,670, 5,304,340, 5,554,120, 5,868,779, 6,746,425, 6,977,103, 6,190,358, 6,605,057, 6,210,364, 6,283,939 and 7,252,650 and pending U.S. Patent Applications, Pub. No.: US 2006/0224115, published on Oct. 5, 2006 and Pub. No.: US 2008/0183132, published on Jul. 31, 2008. Each of said U.S. Patents and said pending patent applications is incorporated, by reference, in this application in its entirety.

The present invention provides novel simpler structures and methods of and apparatus for making reinforced balloons capable of withstanding high internal pressures without excessive dilation. The present invention also provides a method for selecting the reinforcement braid structures and the reinforcement yarn used for making the reinforcement braid.

In accordance with open textile/fibrous structures literature and/or the present invention, jamming is a condition of high fabric packing density where a position of limiting structural geometry is reached due to the inability of solids to interpenetrate during braid, knitted fabric (warp or weft knitted fabrics) or woven fabric formation and/or tensile, compressive and/or shear deformation. In the case of extensive jamming of a tubular braid or a tubular knitted sleeve (warp or weft knitted sleeve), it is the point where structural extension generated by the straightening and/or realignment of the fabric or braid threads in the direction of load stops and extension due to the straining of the strands/threads begins. For compressive jamming it is where strain from similar structural accommodation stops and buckling of the tubular braid or knitted sleeve starts. Also, in accordance with the present invention, the helix angle of a braid is the angle between the helix assumed by the braid element and the axis of the braid.

SUMMARY OF THE INVENTION

The present invention provides a method of and an apparatus for making reinforced medical balloons. The method and the apparatus described may be used for reinforcing any medical balloon by using a hollow fibrous reinforcement sleeve. The sleeve may be in the form of a tubular braid, a tubular warp knitted fabric, a tubular weft knitted fabric or a tubular woven fabric.

BRIEF DESCRIPTION OF THE DRAWING

FIG. 1 is a cross-sectional view of the present invention apparatus used for reinforcing medical balloons.

DESCRIPTION OF THE DRAWING ELEMENTS AND APPARATUS COMPONENTS

FIG. 1 shows an embodiment of an apparatus designed, in accordance with the present invention, for performing the steps of the process of making reinforced medical balloons. Following is a description of the various elements shown in the drawing, FIG. 1, and identified by their respective numbers:

1 Device for making reinforced balloons.
2 Sources of coaxial rotational motion for drive shafts 3. These two rotational motion sources may be separate but equal speed motors or two identical number of teeth gears receiving their drives from the same source, or other rotational motion drive sources known in the art. The directions of rotation of drive shafts 3, as viewed from a point located between them, are opposite to each other so that the balloon, as gripped by grippers 9, would rotate without experiencing any twisting action.
3 Drive shafts.
4 Spring ends anchoring/attaching blocks which are rigidly connected to drive shafts 3 and rotate with and at the same speed as drive shafts 3.
5 Reinforcement sleeve clamps. In one embodiment, these clamps are in the form of radially collapsible collars which clamp on the reinforcement sleeve as they (the clamps) are pulled towards the spring ends anchoring blocks 4. Preferably, sleeve clamps 5 are lined with friction/anti slip liners 6. Alternatively, clamps 5 may be substituted with hooks designed to engage with and axially stretch reinforcement sleeve.
6 Reinforcement sleeve clamp friction/anti slip liners.
7 Tension springs stretching between anchoring blocks 4 and clamps 5. Alternatively, tension springs 7 may be substituted with elastomeric bands or other means known in the art to cause a pulling action on clamps 5 towards anchoring blocks 4.
8 End points of springs 7, shown in the extended state of springs 7.
9 Balloon end clamping grippers.
10 Fulcrums of Grippers 9.

11 Springs acting on gripper handles/levers 13 to cause gripper clamping ends 12 to grip on balloon distal and proximal shafts and the mandrel ends within them.
12 Gripper clamping ends, normally in a closed (gripping) position under the action of springs 11.
13 Gripper handles/levers.
14 Balloon.
14-a Balloon body.
15 Balloon proximal shaft.
15-a Balloon proximal transition zone.
16 Balloon distal shaft.
16-a Balloon distal transition zone.
17 Mandrel, having a diameter not larger than the inner diameter of the balloon distal shaft 16 and a length, as shown in FIG. 1, that is shorter than the end-to-end length of the balloon. The mandrel length, however, must be sufficient to enable grippers 9 to hold on portions of the balloon distal shaft and the balloon proximal shaft containing portions of mandrel 17. In another embodiment, mandrel 17 may have an end 19 having a diameter not larger than the inner diameter of the balloon distal shaft and another end 18 having a diameter larger than the inner diameter of the balloon distal shaft but not larger than the inner diameter of the balloon proximal shaft.
18 Large diameter end of mandrel 17.
19 Small diameter end of mandrel 17.
20 Hermetically sealed ends of pressurized balloon.
21 Reinforcement sleeve, shown for the case of a hollow round braid, in the balloon body portion, in the axially stretched and radially collapsed state.
22 Reinforcement sleeve, shown for the case of a hollow round braid, in the balloon proximal shaft zone, in the axially stretched and radially collapsed state.
23 Reinforcement sleeve, shown for the case of a hollow round braid, in the balloon distal shaft zone, in the axially stretched and radially collapsed state.
24 Yarn or high strength yarn or thin narrow tape package/source.
25 Yarn or high strength yarn or thin narrow tape.
26 Stationery strand/yarn guide.
27 Stationary strand/yarn guide.
28 Traversing wrapping yarn guide covering zones D, B and P shown in FIG. 1, which are the distal shaft zone, transitional and body zones and proximal shaft zone, respectively.
29 Traversing wrapping yarn guide covering the balloon proximal shaft zone, zone P.
30 Traversing wrapping yarn guide covering the balloon distal shaft zone, zone P.
31 Holder of guide 28.
32 Holder of guide 29.
33 Holder of guide 30.
34 Air heater and blower.
35 Hot air
36 Electrical wiring
37 Electrical switch
38 Electrical plug.
39 Hooks positioned around the circumference of clamps 5, (optional). These hooks are adapted for holding yarns held by guide 28 as it (guide 28) traverses back and forth towards and behind hooks 39 to form longitudinal reinforcement elements stretching back and forth from the distal shaft zone to the proximal shaft zone.
40 Arrow showing direction of rotation of gripper 12 gripping distal end 16 of balloon.
41 Arrow showing direction of rotation of gripper 12 gripping proximal end 18 of balloon.

DETAILED DESCRIPTION OF THE INVENTION

In accordance with the present invention, a method is provided for making a reinforced medical balloon, the method comprises the steps of:

providing a monolithic structure balloon, said balloon comprising a balloon body, a proximal shaft, a distal shaft, a proximal transition zone and a distal transition zone, said balloon body having an outer diameter and a wall thickness, a proximal shaft outer diameter and a wall of thickness and a distal shaft outer diameter and a wall thickness, providing a hollow tubular braid made of N reinforcement yarns, said braid being made on a tubular braiding machine utilizing a number of carriers N, a first half of said reinforcement yarns (N/2) forming right hand helices and a second half of said reinforcement yarns (N/2) forming left hand helices, said reinforcement yarns, of said first and said second halves, interlacing in accordance with a predetermined interlacing (weaving/braiding) pattern, said hollow tubular braid having a stress-free (i.e., as produced and laid of a flat surface under no externally applied load) inner diameter, a stress-free helix angle and an axial tension jammed state inner diameter and an axial compression-jammed state inner diameter, said axial compression jammed state inner diameter being larger than said outer diameter of said balloon body and said tensile-jammed state inner diameter being not larger than said outer diameter of said distal shaft, said reinforcement yarns having a tensile breaking stress, a tensile modulus, and a slope/tangent of the initial portion of its stress-strain diagram defining the tangent of an angle, said balloon body having a hoop direction breaking stress and a hoop direction modulus and a slope/tangent of the initial portion of its stress-strain diagram defining the tangent of an angle, said balloon body having an axial direction breaking stress and an axial direction modulus and a slope/tangent of the initial portion of its stress-strain diagram defining the tangent of an angle, said tensile breaking stress of said reinforcement yarns being at least 4 gram per denier (70,466 psi) but preferably not exceeding 8 gram per denier (140,932 psi) and said tensile modulus of said reinforcement yarns being in the range of 50 to 95 gram per denier (880,825-1,673,568 psi) and said hoop direction tensile modulus being equal to said tensile modulus of said reinforcement yarns divided by r, where r is the ratio of said tensile modulus of said reinforcement yarns to said hoop direction modulus of said balloon body, said ratio being at least equal to 4.0, inflating said balloon by introducing a pressurized fluid inside said balloon, thereby increasing its bending rigidity and resistance to lateral collapse, sealing the proximal and distal ends of said balloon, inserting said balloon inside said tubular braid, stretching said braid thereby causing it to collapse around said balloon, apply a radially-acting pressure on the exterior surface of the balloon and conform to the shape of said balloon, including said proximal shaft, said proximal transition zone, said balloon body, said distal transition zone and said distal shaft and forming a reinforcement yarn helix angle, in the zone of said body, in the range of 55 to 85 degrees, bonding said stretched braid to exterior surface of said balloon, deflating said balloon, and trimming/cutting said distal and proximal shafts to desired lengths.

Alternatively and in accordance with the present invention a method is provided for making a reinforced medical balloon, capable of withstanding high internal pressures without bursting and without excessive dilation. The method comprises the steps of;

providing a monolithic structure balloon, said balloon comprising a balloon body, a proximal shaft, a distal shaft, a proximal transition zone and a distal transition zone, and a having an end-to-end balloon length, said balloon body having an outer diameter, an inner diameter and a wall thickness, said proximal shaft having a proximal shaft outer diameter, an inner diameter and a wall thickness and said distal shaft having a distal shaft outer diameter, an inner diameter and a wall thickness, providing a mandrel, said mandrel having a length shorter than said end-to-end full length of said balloon and a diameter not exceeding the inner diameter of said distal shaft, hermetically sealing one end of said balloon, inserting said mandrel through the other end of said balloon, feeding a compressed fluid into said balloon through said other end of said balloon, hermetically sealing said other end of said balloon, thereby having a pressurized balloon containing a mandrel in its interior extending between said one end and said other end, providing a hollow tubular reinforcement sleeve, said sleeve being a hollow tubular braid made of N reinforcement yarns, said braid being made on a tubular braiding machine utilizing a number of carriers N, a first half of said reinforcement yarns (N/2) forming right hand helices and a second half of said reinforcement yarns (N/2) forming left hand helices, said reinforcement yarns, of said first and said second halves, interlacing in accordance with a predetermined interlacing pattern, said hollow tubular braid having a stress-free inner diameter, and an axial tension jammed state inner diameter and an axial compression-jammed state inner diameter, said axial compression jammed state inner diameter being larger than said outer diameter of said balloon body, said reinforcement yarns having a tensile breaking stress, and a tensile modulus, said balloon body having a hoop direction breaking stress and a hoop direction modulus, said tensile breaking stress of said reinforcement yarns being at least 4 gram per denier (70,466 psi) but not exceeding 8 gram per denier (140,932 psi) and said tensile modulus of said reinforcement yarns being in the range of 50 to 95 gram per denier (880,825-1,673,568 psi) and said hoop direction modulus of said balloon body being equal to said tensile modulus of said reinforcement yarns divided by r, where r is the ratio of said tensile modulus of said reinforcement yarns to said hoop direction modulus of said balloon body, said ratio being at least equal to 4.0, thereby increasing its bending rigidity and resistance to lateral collapse, sealing the proximal and distal ends of said balloon, inserting said balloon inside said tubular sleeve, providing a device comprising:

two spaced apart coaxial drive shafts, each of said coaxial drive shafts connected to a source of rotational motion capable of simultaneously rotating at the same speed but opposite directions of rotation, as viewed from a point located between said drive shafts, each of said drive shafts having a spring anchoring block rigidly attached to it and located near said source of rotational motion, said anchoring block being connected to a reinforcement sleeve clamp by at least one tension spring extending between said anchoring block and said reinforcement sleeve clamp, and a balloon end gripper rigidly attached to it coaxially extending beyond the free end of said drive shaft, said gripper having a fulcrum, a release handle and a gripping end which is normally closed under the action of a spring, at least one yarn guide located between said balloon end grippers, a reinforcement yarn source and yarn guides that guide said reinforcement yarn from said source to said at least one yarn guide, and a source of hot air located in the area between said grippers, placing said balloon and reinforcement sleeve between said grippers and gripping the ends of said balloon containing said mandrel by said clamping ends of said gripper, using said reinforcement sleeve clamps, stretching said braid thereby causing it to collapse around said balloon, apply a radially-acting pressure on the exterior surface of the balloon and conform to the shape of said balloon, including said proximal shaft, said proximal transition zone, said balloon body, said distal transition zone and said distal shaft and forming a reinforcement yarn helix angle, in the zone of said body, in the range of 55 to 85 degrees, winding said reinforcement yarn at lease around said distal shaft and said proximal shaft by activating said sources of rotational motion and traversing said yarn guide to cover said distal shaft and proximal shaft with circumferential wrappings of said reinforcement yarn, applying at least on coating of a bonding adhesive onto said balloon and said reinforcement sleeve to bond said balloon, said reinforcement sleeve and said circumferential wrappings of said reinforcement yarn and form a reinforced balloon, activating said source of hot air in order to cure said bonding adhesive, releasing said sleeve clamps and said grippers, removing said reinforced balloon, and cutting off said sealed ends, and removing said mandrel.

The invention claimed is:

1. A method of making a reinforced medical balloon, capable of withstanding high internal pressures without bursting and without excessive dilation, comprising the steps of;

providing a monolithic structure balloon, said balloon comprising a balloon body, a proximal shaft, a distal shaft, a proximal transition zone and a distal transition zone, and a having an end-to-end full balloon length, said balloon body having an outer diameter, an inner diameter and a wall thickness, said proximal shaft having a proximal shaft outer diameter, an inner diameter and a wall thickness and said distal shaft having a distal shaft outer diameter, an inner diameter and a wall thickness, providing a mandrel, said mandrel having a length shorter than said end-to-end full length of said balloon and a diameter not exceeding the inner diameter of said distal shaft, hermetically sealing one end of said balloon, inserting said mandrel through the other end of said balloon, feeding a compressed fluid into said balloon through said other end of said balloon, hermetically sealing said other end of said balloon, thereby having a pressurized balloon containing a mandrel in its interior extending between said one end and said other end, providing a hollow tubular reinforcement sleeve, said sleeve being a hollow tubular braid made of N reinforcement yarns, said braid being made on a tubular braiding machine utilizing a number of carriers N, a first half of said reinforcement yarns (N/2) forming right hand helices and a second half of said reinforcement yarns (N/2)

forming left hand helices, said reinforcement yarns, of said first and said second halves, interlacing in accordance with a predetermined interlacing pattern, said hollow tubular braid having a stress-free inner diameter, and an axial tension jammed state inner diameter and an axial compression-jammed state inner diameter, said axial compression-jammed state inner diameter being larger than said outer diameter of said balloon body, said reinforcement yarns having a tensile breaking stress, and a tensile modulus, said balloon body having a hoop direction breaking stress and a hoop direction modulus, said tensile breaking stress of said reinforcement yarns being at least 4 gram per denier (70,466 psi) but not exceeding 8 gram per denier (140,932 psi) and said tensile modulus of said reinforcement yarns being in the range of 50 to 95 gram per denier (880,825-1,673,568 psi) and said hoop direction modulus of said balloon body being equal to said tensile modulus of said reinforcement yarns divided by r, where r is the ratio of said tensile modulus of said reinforcement yarns to said hoop direction modulus of said balloon body, said ratio being at least equal to 4.0, thereby increasing its bending rigidity and resistance to lateral collapse, sealing the proximal and distal ends of said balloon, inserting said balloon inside said tubular sleeve, providing a device comprising:

two spaced apart coaxial drive shafts, each of said coaxial drive shafts connected to a source of rotational motion capable of simultaneously rotating at the same speed but opposite directions of rotation, as viewed from a point located between said drive shafts, each of said drive shafts having a spring anchoring block rigidly attached to it and located near said source of rotational motion, said anchoring block being connected to a reinforcement sleeve clamp by at least one tension spring extending between said anchoring block and said reinforcement sleeve clamp, and a balloon end gripper rigidly attached to it coaxially extending beyond the free end of said drive shaft, said gripper having a fulcrum, a release handle and a gripping end which is normally closed under the action of a spring, at least one yarn guide located between said balloon end grippers, a reinforcement yarn source and yarn guides that guide said reinforcement yarn from said source to said at least one yarn guide, and a source of hot air located in the area between said grippers, placing said balloon and reinforcement sleeve between said grippers and gripping the ends of said balloon containing said mandrel by said clamping ends of said gripper, using said reinforcement sleeve clamps, stretching said braid thereby causing it to collapse around said balloon, apply a radially-acting pressure on the exterior surface of the balloon and conform to the shape of said balloon, including said proximal shaft, said proximal transition zone, said balloon body, said distal transition zone and said distal shaft and forming a reinforcement yarn helix angle, in the zone of said body, in the range of 55 to 85 degrees, winding said reinforcement yarn at lease around said distal shaft and said proximal shaft by activating said sources of rotational motion and traversing said yarn guide to cover said distal shaft and proximal shaft with circumferential wrappings of said reinforcement yarn, applying at least on coating of a bonding adhesive onto said balloon and said reinforcement sleeve to bond said balloon, said reinforcement sleeve and said circumferential wrappings of said reinforcement yarn and form a reinforced balloon, activating said source of hot air in order to cure said bonding adhesive, releasing said sleeve clamps and said grippers, removing said reinforced balloon, cutting off said sealed ends, and removing said mandrel.

\* \* \* \* \*